US009364450B2

(12) United States Patent
Kobel-Buys

(10) Patent No.: US 9,364,450 B2
(45) Date of Patent: Jun. 14, 2016

(54) CLENBUTEROL FOR USE IN TREATMENT OF AUTISM

(75) Inventor: Krystyna Kobel-Buys, Strzelin (PL)

(73) Assignees: STOWARZYSZENIE SW. CELESTYNA, Strzelin (PL); KRYSTYNA KOBEL-BUYS, Strzelin (PL)

( * ) Notice: Subject to any disclaimer, the term of this patent is extended or adjusted under 35 U.S.C. 154(b) by 37 days.

(21) Appl. No.: 14/123,555

(22) PCT Filed: May 30, 2012

(86) PCT No.: PCT/PL2012/050014
§ 371 (c)(1), (2), (4) Date: Dec. 3, 2013

(87) PCT Pub. No.: WO2012/165984
PCT Pub. Date: Dec. 6, 2012

(65) Prior Publication Data

US 2014/0107215 A1 Apr. 17, 2014

(30) Foreign Application Priority Data

Jun. 3, 2011 (PL) ........................................ 395112

(51) Int. Cl.
*A61K 31/136* (2006.01)
*A61K 31/137* (2006.01)

(52) U.S. Cl.
CPC ............. *A61K 31/136* (2013.01); *A61K 31/137* (2013.01)

(58) Field of Classification Search
CPC ........................... A61K 31/136; A61K 31/137
See application file for complete search history.

(56) References Cited

U.S. PATENT DOCUMENTS 5,530,029 A 6/1996 Maltin .......................... 514/653
5,552,442 A 9/1996 Maltin .......................... 514/620
2002/0028510 A1* 3/2002 Sanberg ............... C12N 5/0618 435/368
2004/0248984 A1* 12/2004 Krieglstein et al. ........... 514/620
2005/0222272 A1 10/2005 Chez ............................ 514/662
2008/0014152 A1 1/2008 Di Mauro et al. ............... 424/45
2010/0130566 A1 5/2010 Purpura et al. ................ 514/362

FOREIGN PATENT DOCUMENTS

EP 0 308 157 A2 3/1989 ........... A61K 31/135
EP 0 662 324 A1 7/1995 ........... A62K 31/135
WO WO 01/68137 A2 9/2001
WO WO 2008/095253 A1 8/2008 ............. A61P 25/18

OTHER PUBLICATIONS

Knabe et al., Letter to the Editor, Journal of Autism and Developmental Disorders, vol. 20, No. 4, 1990, pp. 591-593.*

*Establishing a basis for clenbuterol treatment of some diseases of the CNS*; Brzecki; New Medicine 2003 PL; vol. 6, No. 1, 2003; pp. 29-34.

*A comparison of the neurochemical and behavioral effects of clenbuterol and desipramine*; Finnegan et al.; European Journal of Pharmacology; vol. 134, No. 2, 1987; pp. 131-136.

International Search Report mailed Aug. 27, 2012 in corresponding application No. PCT/PL2012/050014.

Written Opinion mailed Aug. 27, 2012 in corresponding application No. PCT/PL2012/050014.

Search Report mailed Jul. 18, 2011 in corresponding application No. P.395112.

Communication under Rule 71(3) EPC mailed Jan. 29, 2015 in corresponding application No. 12 730 052.3 (inclusive of marked-up allowed specification, including allowed claims).

* cited by examiner

*Primary Examiner* — Sreeni Padmanabhan
*Assistant Examiner* — Jody Karol
(74) *Attorney, Agent, or Firm* — Renner Kenner Greive Bobak Taylor & Weber

(57) ABSTRACT

Clenbuterol or its salt for use in the treatment of autism, in particular pediatric autism. Improved contact with surroundings, better concentration, improved ability to plan a specific task, improved understanding, calming, and reduced psychomotor anxiety were observed.

9 Claims, No Drawings

CLENBUTEROL FOR USE IN TREATMENT OF AUTISM

CROSS-REFERENCE TO RELATED APPLICATION

This is a §371 application of International patent application number PCT/PL2012/050014 filed May 30, 2012, which claims the benefit of Polish patent application number P.395112 filed on Jun. 3, 2011, and which is incorporated herein by reference.

TECHNICAL FIELD

The invention relates to clenbuterol for a new use in treatment of autism, in particular pediatric autism.

BACKGROUND ART

Studies in children indicate that the autism spectrum is a moderately frequent, heterogeneous range of conditions classified as pervasive developmental disorders, present in 3-6 per 1,000 live-born children. Autism is characterized by abnormalities in 3 domains: 1. social integration, 2. language, communication and play, 3. scope of interests and activities. These developmental disorders pose a major social problem. An increasing incidence of autism in recent years has stimulated research on new treatment options for this syndrome. Pedagogic, psychological and speech therapy methods constitute an essential part of the therapy, while psychomotoric and sensomotoric methods are supplementary. Recent years have seen a progress in research on pharmacological methods of treatment of autism and its symptoms. Studies focused on administration of medications which proved effective in treatment of certain symptoms and behaviors observed also in people with autism, such as attention disorders, anxiety, and hyperactivity. Medications applied were selective monoamines reuptake inhibitors (clomipramine, fluvoxamine, fluoxetine, paroksetine and sertraline), used in treatment of certain symptoms coexisting with autism, such as depression, anxiety, and obsessive-compulsive activities.

Over recent years the most commonly investigated medications in the context of treatment of autism were antipsychotics which reduce hyperactivity, stereotyped behaviors, withdrawal and aggression in autistic children. The most commonly used medications in this group include aripiprazole, risperidone and olanzapine. Unfortunately, just like antidepressants, these medications produce adverse effects, including reduced activity and sedation.

Stimulants were also used in order to decrease hyperactivity of autistic children; however, contrary adverse effects were often observed.

Patent application US2005222272 reveals a method of treatment of autism, including administration of an effective amount of a medication described as NMDA (N-methyl-D-aspartate activated) receptor antagonist or its pharmaceutically acceptable salt, preferably at doses from about 1 mg to about 100 mg daily. Application of several compounds of this group improved frontal executive functions related to symptoms of autism, including speech expression, and reduced perseveration.

Patent application US20100130566 concerns treatment of autism spectrum disorder (ASD), including autism, using agents activating locus coeruleus-noradrenergic (LC-NA) system in the brain. However, no examples of specific effects of this treatment are provided in the document.

SUMMARY OF THE INVENTION

Unexpectedly, it turned out that administration of effective amounts of clenbuterol or its pharmaceutically effective salt seems to practically alleviate functional disorders related to ASD. In addition, no adverse effects associated with medications previously used in treatment of autism were observed with a long-term administration of clenbuterol or its pharmaceutically acceptable salt.

Clenbuterol ((RS)-1-(4-amino-3,5-dichlorophenyl)-2-(tert-butylamino)ethanol) is a $\beta_2$-adrenergic receptor agonist. When present in the blood, it stimulates adrenergic receptors in muscles and increases metabolism of carbohydrates and fats as well as metabolism and synthesis of proteins in striated muscles. Apart from its known (and applied in treatment) activity on smooth muscles of the bronchial tree and blood vessels, clenbuterol increases the mass and strength of muscles.

In recent years, central neuroprotective activity of this $\beta_2$-adrenomimetic has been confirmed in children with central movement disorders in the course of cerebral palsy. The effects of clenbuterol on the central nervous system include modulation of neurotransmitters, regulation of cell metabolism and stabilization of cell membranes. In this way it may improve certain neuropsychological disorders.

The aim of this invention is to provide an efficacious and safe method of alleviation and treatment of autistic symptoms, free of adverse effects.

BEST MODE FOR CARRYING OUT THE INVENTION

The subject of the invention is clenbuterol or its pharmaceutically acceptable salt for use in the treatment of symptoms of autism, in particular pediatric autism. The most commonly used salt of clenbuterol is its hydrochloride.

Treated symptoms of autism include a lack of contact with surroundings, poor understanding, a lack of concentration and ability to plan, speech and attention disorders, and psychomotor anxiety.

Clenbuterol or its salt is used in an oral or inhaled formulation. Oral formulations include tablets, powder, granules, pellets, capsules, solution, and syrup.

According to the invention, clenbuterol or its salt is administered at a daily dose from 0.1 to 1.5 μg per kilogram of the patient's bodyweight, preferably at a daily dose from 0.2 μg to 1.2 μg per kilogram of the patient's bodyweight, preferably at a daily dose from 0.2 μg to 0.5 μg per kilogram of the patient's bodyweight.

The daily dose of clenbuterol or its salt may be administered as one dose or divided into two doses.

In order to achieve optimum results, clenbuterol or its salt is administered for a period from 1 to 24 months, preferably from 3 to 12 months.

The method of control and alleviation of autistic symptoms according to the invention comprises administration of an effective amount of clenbuterol or its pharmaceutically acceptable salt, preferably hydrochloride, to the patient. Clenbuterol is administered orally or inhaled; preferably, oral formulation is selected from the following: tablets, powder, granules, pellets, capsules, solution, or syrup.

In the method of the invention, clenbuterol or its salt is administered at a daily dose from 0.1 to 1.5 μg per kilogram of the patient's bodyweight, preferably at a daily dose from 0.2 μg to 1.2 μg per kilogram of the patient's bodyweight, preferably at a daily dose from 0.2 μg to 0.5 μg per kilogram of the patient's bodyweight. These doses are different from hitherto applied doses of clenbuterol.

In the method of the invention, the medication is administered in one or two doses per day. Clenbuterol or its salt is administered for a period from 1 to 24 months, preferably from 3 to 12 months.

New use of clenbuterol or its salts in production of a medication for treatment of autistic symptoms in preferred embodiments is presented in more detail in the following examples.

EXAMPLES

Example 1

A 4-year old patient with autistic symptoms in the form of disorders of social integration, verbal and non-verbal communication, play disorders and concomitant anxiety, especially when changing environment, was administered clenbuterol at a dose of ¼ tablet containing 20 μg of clenbuterol once daily for a period of 3 months. After application of the therapy the increased interest in the environment was observed; the child's contact with surroundings improved and its anxiety symptoms decreased.

Example 2

A 7-year old patient with pediatric autism and cerebral palsy was administered the medication at a dose of ¼ of 20 μg tablet twice daily for a period of 12 months. The applied treatment resulted in improvement with respect to understanding, concentration, attention, and speech.

Example 3

A 9-year old patient with early pediatric autism, psychomotor hyperactivity syndrome and speech development delay was administered clenbuterol at a dose of ¼ of 20 μg tablet once daily for a period of 12 months. Improvement in speech expression was achieved as well as reduction of psychomotor anxiety and grimacing.

It has been assumed that clenbuterol, modulating the brain neurotransmitter systems, affects also the endocrine and immunological system. As a result, alleviation of communication disorders and improved contact with surroundings is observed in autistic children. Improved contact with surroundings, better concentration, improved ability to plan a specific task, improved understanding, calming, and reduced psychomotor anxiety were observed during administration of clenbuterol at very small doses to autistic children.

The invention claimed is:

1. A method of control and alleviation of one or more symptoms of autism in a patient, wherein the symptoms are selected from the group consisting of a lack of contact with surroundings, poor understanding, a lack of concentration, a lack of ability to plan, and speech and attention disorders, the method comprising administering an effective amount of clenbuterol or its pharmaceutically acceptable salt.

2. The method of claim 1, wherein clenbuterol or its salt is administered orally or inhaled.

3. The method of claim 2, wherein clenbuterol or its salt is administered orally in the form selected from among tablets, powder, granules, pellets, capsules, solution, or syrup.

4. The method of claim 2, wherein clenbuterol or its salt is administered at a daily dose from 0.1 μg to 1.5 μg per kilogram of the patient's bodyweight.

5. The method of claim 4, wherein clenbuterol or its salt is administered at a daily dose of from 0.2 μg to 1.2 μg per kilogram of the patient's bodyweight.

6. The method of claim 4, wherein clenbuterol or its salt is administered in one or two doses per day.

7. The method of claim 6, wherein clenbuterol or its salt is administered for a period from 1 to 24 months.

8. The method of claim 1, wherein the pharmaceutically acceptable salt of clenbuterol is clenbuterol hydrochloride.

9. The method of claim 5, wherein clenbuterol or its salt is administered at a daily dose of from 0.2 μg to 0.5 μg per kilogram of the patient's bodyweight.

* * * * *